United States Patent
Zehnder et al.

(10) Patent No.: US 8,221,469 B2
(45) Date of Patent: Jul. 17, 2012

(54) PEDICLE SCREW WITH A CLOSURE DEVICE FOR SECURING A ROD FOR STABILIZATION OF THE VERTEBRAL COLUMN

(75) Inventors: Thomas Zehnder, Bäch (CH); Reto Braunschweiler, Neftenbach (CH)

(73) Assignee: Spinelab AG, Zug (CH)

( * ) Notice: Subject to any disclaimer, the term of this patent is extended or adjusted under 35 U.S.C. 154(b) by 567 days.

(21) Appl. No.: 12/318,326

(22) Filed: Dec. 24, 2008

(65) Prior Publication Data

US 2009/0171401 A1 Jul. 2, 2009

(30) Foreign Application Priority Data

Dec. 31, 2007 (EP) .................................... 07150489

(51) Int. Cl.
*A61B 17/70* (2006.01)
(52) U.S. Cl. ........................ 606/265; 606/264
(58) Field of Classification Search .................. 606/264, 606/265
See application file for complete search history.

(56) References Cited

U.S. PATENT DOCUMENTS

| | | | |
|---|---|---|---|
| 7,294,128 B2 | 11/2007 | Alleyne et al. | |
| 2002/0116001 A1* | 8/2002 | Schafer et al. | 606/61 |
| 2003/0125741 A1* | 7/2003 | Biedermann et al. | 606/61 |
| 2003/0187434 A1 | 10/2003 | Lin | |
| 2005/0171542 A1* | 8/2005 | Biedermann et al. | 606/61 |
| 2006/0173456 A1* | 8/2006 | Hawkes et al. | 606/61 |

FOREIGN PATENT DOCUMENTS

| | | |
|---|---|---|
| DE | 94 03 231 | 6/1994 |
| EP | 1 234 547 | 8/2002 |
| EP | 1795134 A1 * | 6/2007 |
| EP | 1 815 812 | 8/2007 |
| WO | WO 95/01132 | 1/1995 |
| WO | WO 2005/102195 | 11/2005 |
| WO | WO 2007/130840 | 11/2007 |

OTHER PUBLICATIONS

European Search Report dated Jun. 2, 2008.

* cited by examiner

*Primary Examiner* — Bruce E Snow
*Assistant Examiner* — Melissa Hoban
(74) *Attorney, Agent, or Firm* — Jacobson Holman PLLC

(57) ABSTRACT

A pedicle screw with a closure device for securing a rod for stabilization of the vertebral column comprises a screw-in part with a head part, a U-shaped recess in the head part., in which recess the rod is held by the closure device. The closure device comprises a yoke-shaped locking element, which has a collar with a projection on each of the two opposite end regions. One groove is provided on each of the two arms in such a way that the locking element is rotatably placed on the arms. The projections are inserted in the grooves to achieve locking position. A tension screw is screwed into the locking element and rotatably connected to a tension element inserted between the arms, and, in the locked state of the locking element, is able to be tensioned, by means of the tension screw, against the rod inserted in the recess.

9 Claims, 4 Drawing Sheets

Figures 1, 2:
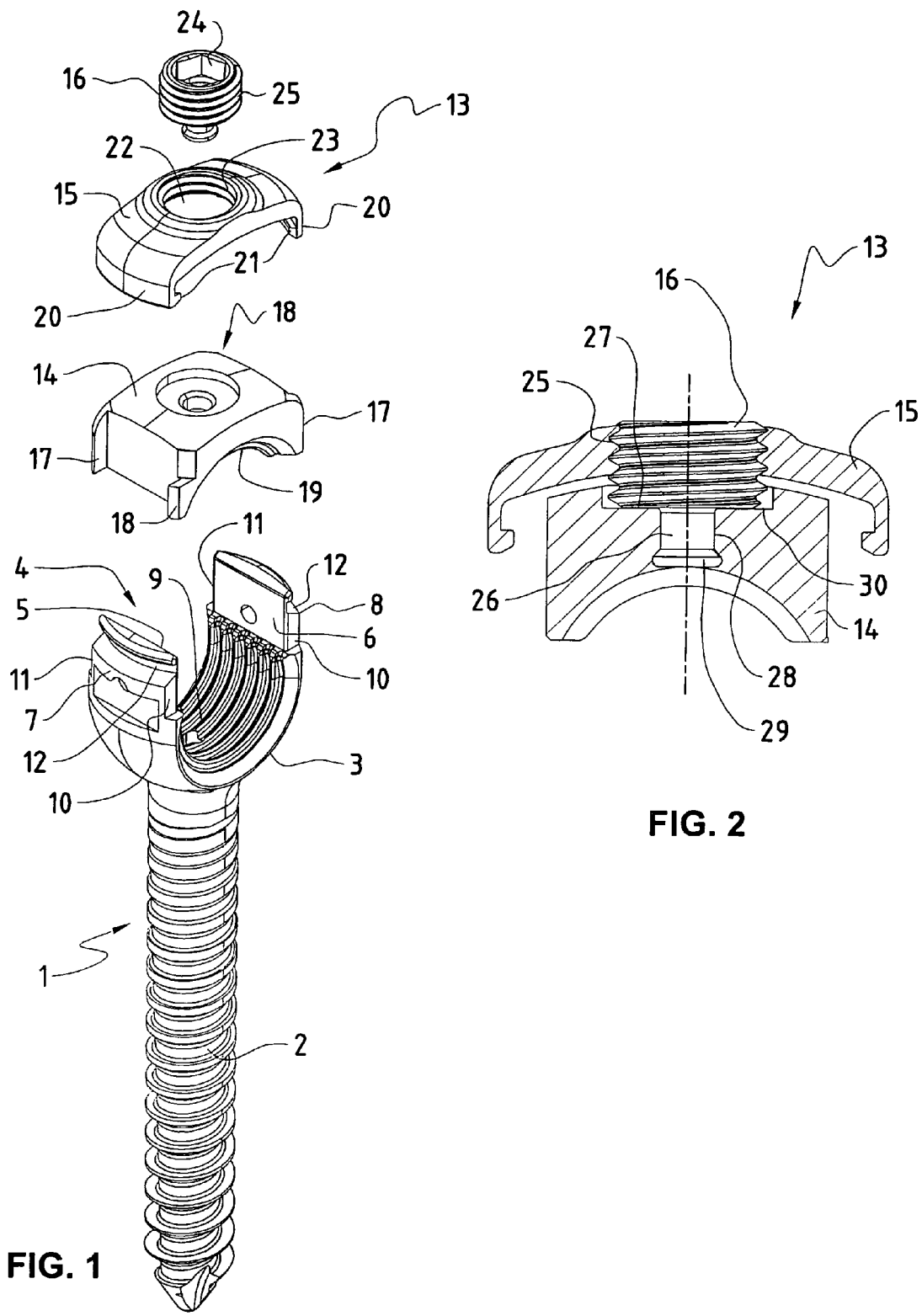

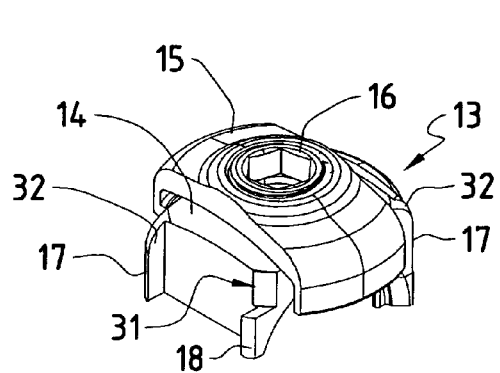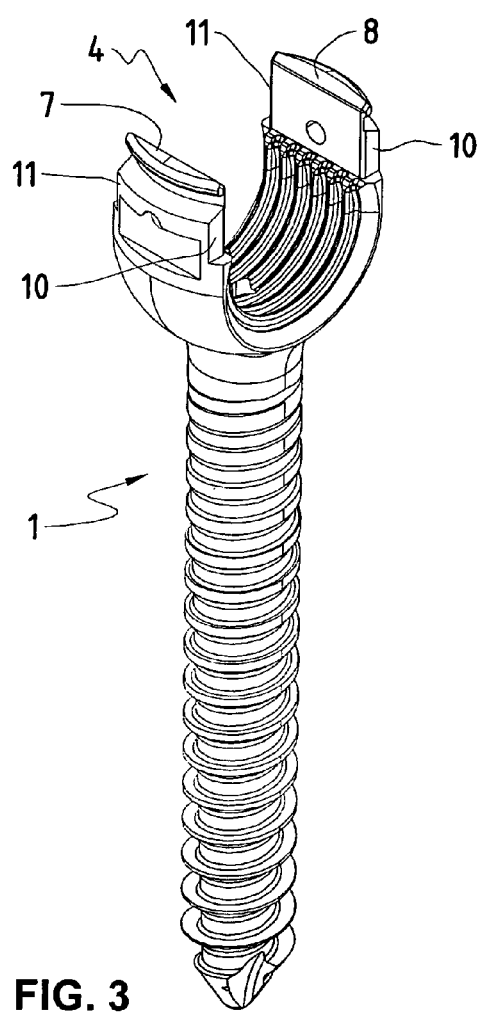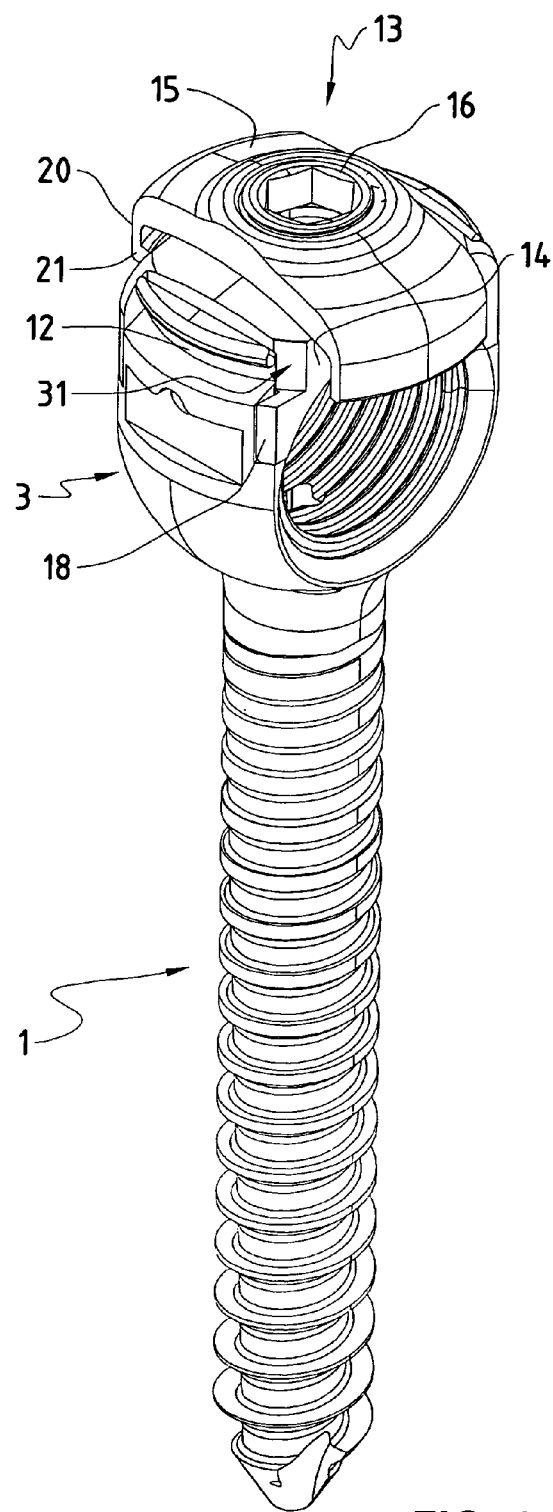
FIG. 3
FIG. 4

PEDICLE SCREW WITH A CLOSURE DEVICE FOR SECURING A ROD FOR STABILIZATION OF THE VERTEBRAL COLUMN

The present invention relates to a pedicle screw with a closure device for securing a rod for stabilization of the vertebral column, comprising a screw-in part, a head part provided on the screw-in part, a U-shaped recess disposed in the head part, which recess is formed by the inner surfaces of two arms and a bottom surface connecting the two inner surfaces, in which recess the rod is insertable and is held by the closure device.

Pedicle screws with a closure device for securing a rod are known from the state of the art in diverse designs. These screws serve to stabilize the vertebral column of patients who have severely damaged vertebral columns. For stabilization, one pedicle screw each is screwed into a number of vertebral bodies, and a rod is placed in the head parts of these pedicle screws, which rod is then connected in each case to the respective pedicle screw, closure devices being used for this purpose. Two different forms of stabilization can be achieved, depending upon which type of rod is used. With use of a rigid rod, a stiffening of the affected vertebral bodies is achieved. When a supportive stabilization of the vertebral bodies is supposed to be achieved, an elastic rod is used, enabling a certain flexibility to be permitted between the individual vertebral bodies.

Regardless of which system is used, an optimal connection between inserted rods and pedicle screws is to be aimed for, which is supposed to be achieved through the closure devices used.

Known from EP-B-1 119 304 is a device for securing spinal rods, which device consists of a pedicle screw having a head portion and a U-shaped recess, in which the rod to be secured is inserted. Serving as closure device is a rotatable element with two laterally protruding projections opposite each other, which have a helical inclination. Through turning of this rotational element, these projections end up in corresponding slot-shaped recesses of the two arms of the U-shaped recess. By turning this rotational element, the rod is held in a clamped way. In order to be able to prevent a release of this rotational element, the clamping surface facing the rod is provided with transversely running recesses which are supposed to engage in the surface of the rod upon reaching of the clamping position.

This device is simple to operate. It is difficult, however, with the predetermined positions of the recesses which are supposed to engage in the rod, to obtain the right tensional force for the rod to be held in the pedicle screw in an optimal way. In addition, there is the risk that the two arms are pressed apart elastically by the projections of the rotational element, which could interfere with the desired tensional force.

The object of the present invention is therefore to create a pedicle screw with a closure device for securing a rod for stabilization of the vertebral column which is easy to manipulate and with which the desired and optimal tensional force can be achieved with any type of rods used.

This object is achieved according to the invention in that the closure device comprises a yoke-shaped locking element having a collar at each of the two end regions opposite each other, on each of which collars projections are provided, directed toward each other. Outside on each of the two arms a groove is provided, running transversely to these arms, such that the yoke-shaped locking element is placeable on the arms and is rotatable, and, to reach the locking position, the projections each end up in the corresponding groove. A tension screw is screwable into the yoke-shaped locking element, which tension screw is connected in a rotatable way to a tension element, which tension element is insertable in a guided way between the arms, and, in the locked state of the locking element, is able to be tensioned, by means of the tension screw, against the rod inserted in the recess.

This closure device is very easy to operate. In particular, a pre-assembled closure device with the locking element, tension screw screwed therein, and tension element connected thereto allows itself to be put as a unit on the pedicle screw. The tension element, with which the tension screw, screwed into the locking element, is rotatably connected, is guided between the arms forming the U-shaped recess of the pedicle screw for receiving the rod, and is moved in after insertion of the rod. The locking element is brought into the locking position by rotation. The tension screw can be tightened, so that the tension element is pressed with the desired force against the rod to be secured. Achieved by pressing the tension element against the rod is that the projections of the locking element are pressed with the corresponding counterforce against the corresponding surfaces of the respective groove, so that the locking element is also secured by friction locking, and a turning back of the locking element is made impossible.

The locking position of the yoke-shaped locking element is preferably determined by stops in the head part. It is thereby ensured that the correct locking position of the yoke-shaped locking element is achieved.

The tension element is preferably provided with guides, by means of which the tension element is placeable in a guided way on the two arms of the head part, which contributes to simplification of operation.

These guides preferably consist of guide ribs provided on the tension element that co-operate with guide surfaces provided on the arms, whereby manufacture of the corresponding elements becomes very easy.

This rotatable connection between tension screw and tension element is preferably achieved by the tension screw having a threaded part which is extended by a bolt piece, and by a support surface being formed between threaded part and bolt piece. To receive the bolt piece, the tension element is provided with a central bore. The end region of the bolt piece remote from the threaded part is provided with a swelling, which can be achieved in a simple and advantageous way by bending up this end region to form a kind of flange.

The support surface is preferably supported on a surface correspondingly provided on the tension element, whereby an optimal transfer of the tension forces is achievable.

A further advantageous embodiment of the invention consists in the rod being made of an elastic material, the cylindrical surface of which is provided with ridges and grooves, and the bottom surface, connecting the inner surfaces of the arms, and the surface of the yoke-shaped locking element facing the rod are provided with corresponding ridges and grooves. Thereby achieved is an optimal formfitting connection between rod and pedicle screw, which is particularly advantageous when the rod is made of an elastic material, for instance a biocompatible plastic, in particular a polyurethane-based material.

An embodiment of the invention will be explained more closely in the following, by way of example, with reference to the attached drawing.

Figure 5:
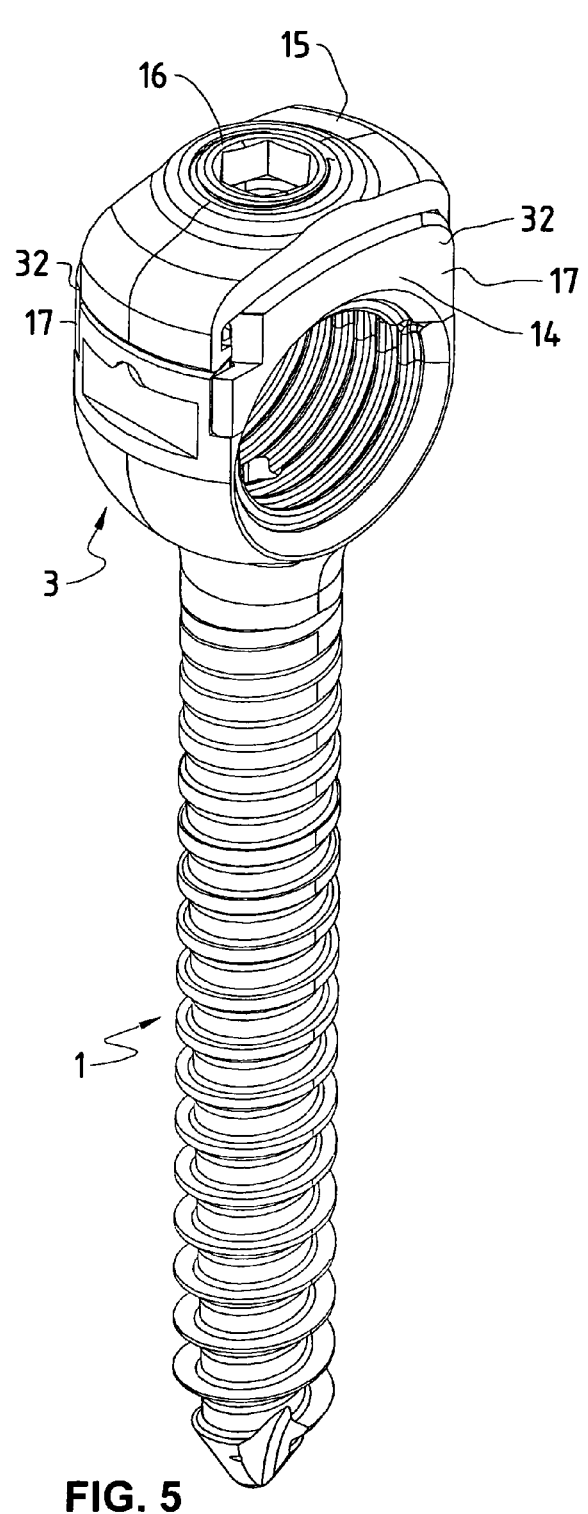
Figure 6:
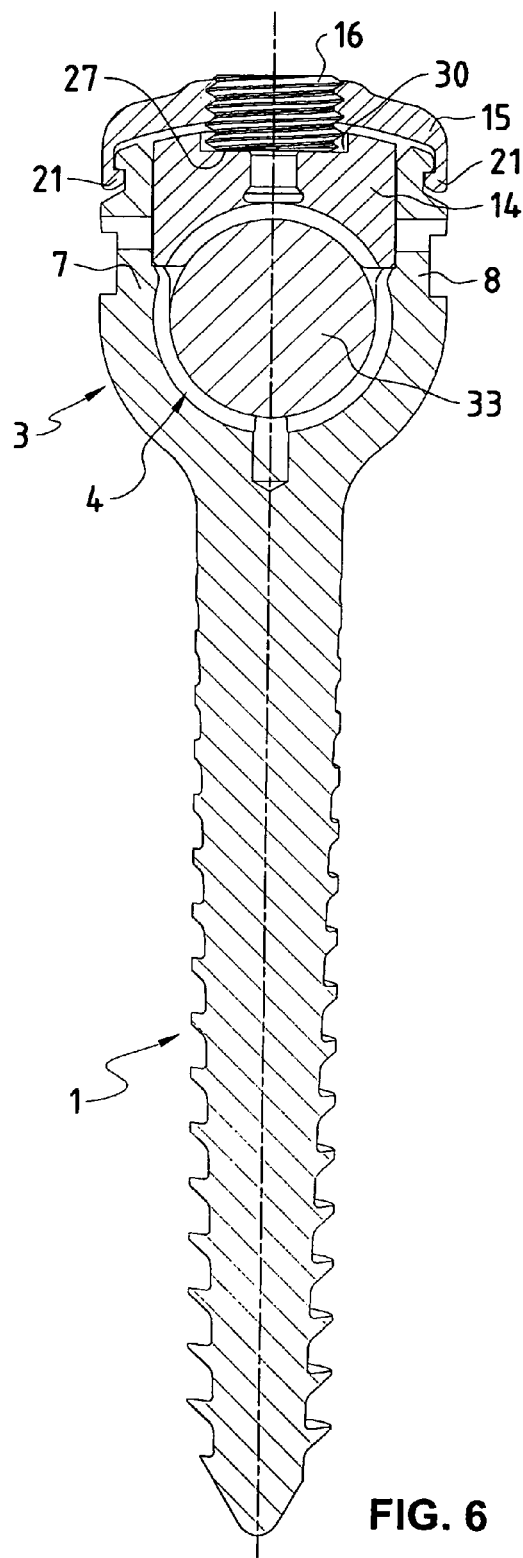
Figure 7:
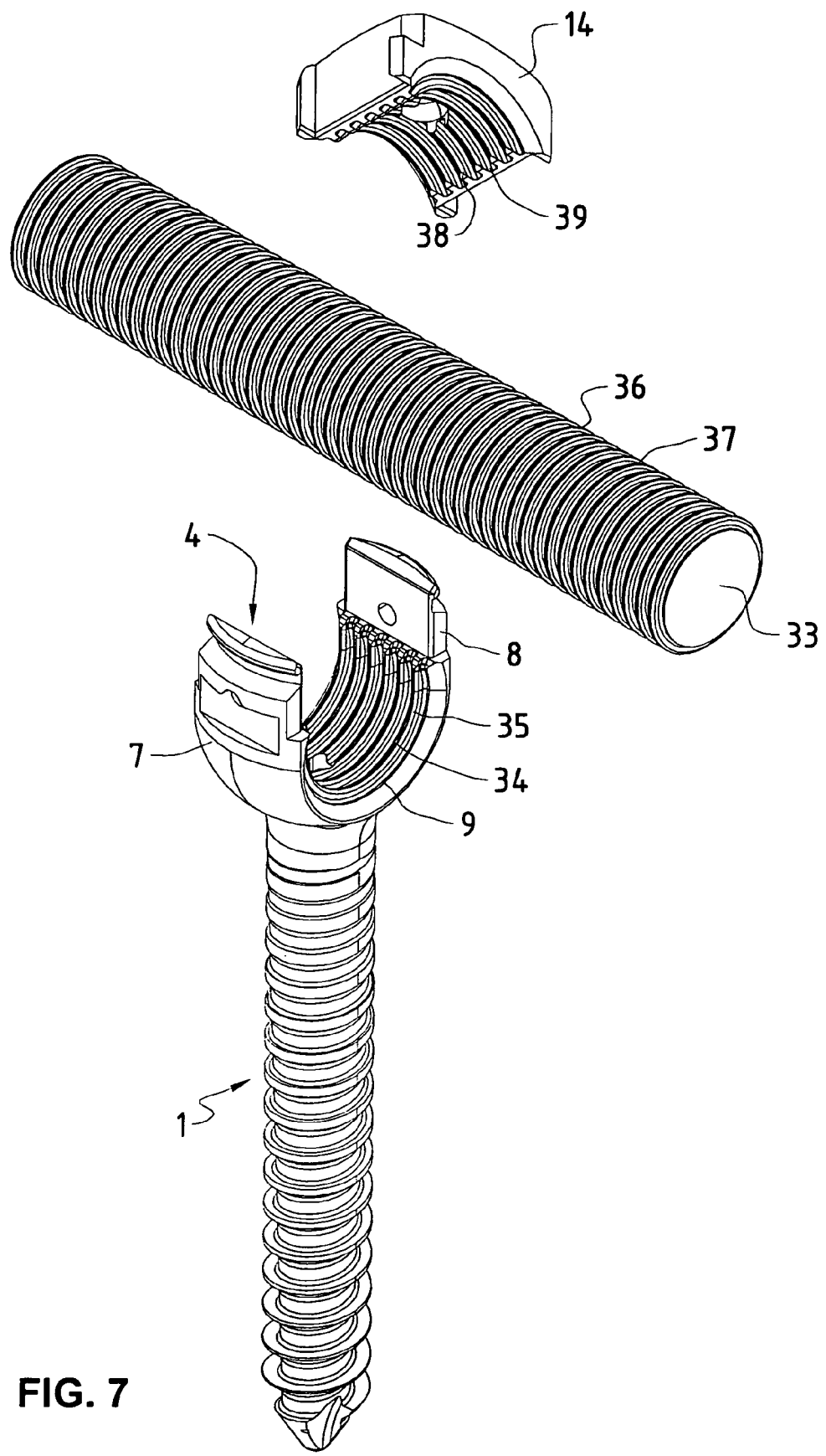

Shown are:

FIG. 1, in a three-dimensional representation, a pedicle screw with a closure device, made up of a tension element, a locking element and the tension screw, in disassembled state;

FIG. 2, in section, a representation of the closure device according to FIG. 1 in connected state;

FIG. 3, in a three-dimensional representation, the pedicle screw with closure device ready to be put on;

FIG. 4, in a three-dimensional representation, the pedicle screw with closure device put on, ready to lock;

FIG. 5, in a three-dimensional representation, the pedicle screw with closure device put on and locked;

FIG. 6, a sectional drawing through the pedicle screw with closure device put on and locked; and FIG. 7, in a three-dimensional representation, the pedicle screw, the rod to be inserted in the pedicle screw, and the tension element.

As can be seen from FIG. 1, the pedicle screw 1 consists of a screw-in part 2 provided with a threading, with which the pedicle screw 1 can be screwed into a vertebral body of a vertebral column of a patient in a known way. Provided on this screw-in part 2 is a head part 3, which is provided with a U-shaped recess 4. This U-shaped recess 4 is formed by the inner surfaces 5, 6 of two arms 7, 8 which are provided on the screw-in part 2. The two inner surfaces 5 and 6 of these two arms are connected to each other through a bottom surface 9, which bottom surface 9 is adapted to the shape of the rod to be inserted in this U-shaped recess 4, as will still be seen later on.

The two lateral regions of the respective arms 7 and 8 are each provided with a guide surface 10, 11. Provided in the upper region of the two arms 7 and 8 on the outside is one groove 12 each, running transversely to these arms. The floor of the groove and the surfaces adjacent to the groove 12 are of circular design.

The U-shaped recess 4 of the head part 3 of the pedicle screw 1 can be closed by a closure device 13. This closure device 13 is composed of a tension element 14, a locking element 15 and a tension screw 16. The tension element 14 allows itself to be inserted between the two arms 7 and 8. For this purpose, this tension element 14 is provided with two guide ribs 17 and 18 each, opposite each other, which, together with the guide surfaces 10 and 11 of the two arms 7 and 8, form the guide. The surface 19 of the tension element 14 turned toward the bottom surface 9 likewise has a shape adapted to the form of the rod.

The locking element 15 has the shape of a yoke, and is provided with a collar 20 on each of the two end regions opposite each other. Provided on each of these collars 20 is a projection 21, which projections are directed toward each other. In addition, the locking element 15 is provided with a bore 22 that is provided with a threading 23. The tension screw 16 is able to be screwed into the threading 23 of this bore 22, which tension screw is provided with a hexagonal socket 24. With this closure device 13, the U-shaped recess 4 in the head part 3 of the pedicle screw 1 can be closed; the rod inserted in this U-shaped recess is thereby securely held, as will still be seen later on.

As can be seen from FIG. 2, the closure device 13 is put together to form a unit. The tension screw 16 is provided with a threaded part 25, on which a bolt piece 26 is attached. A support surface 27 is formed between the threaded part 25 and the bolt piece 26. The bolt piece 26 projects into a central bore 28 made in the tension element 14. The end region of the bolt piece 26 remote from the threaded part 25 is provided with a swelling 29, which can be achieved, for example, by bending up the end region of this bolt piece 26 to form a kind of flange, which bending-up step can be carried out after insertion of the tension screw 16 in the tension element 14. The tension screw 16 and the tension element 14 are thus connected to each other in a way rotatable about the bolt piece 26. The support surface 27 of the tension screw 16 supports itself on a surface 30 provided in a corresponding way on the tension element 14. The tension screw 16 with the tension element connected thereto is then able to be screwed into the locking element 15, whereby the closure device 13 forms a unit.

This closure device 13, put together to form a unit, then allows itself to be put on the head part 3 of the pedicle screw 1. As can be seen from FIG. 3, the locking element 15 is aligned for this purpose transversely with respect to the tension element 14. The closure device 13 can then be moved into the U-shaped recess 4 of the pedicle screw. To accomplish this, the guide ribs 17 and 18 of the tension element 14 are guided by the guide surfaces 10 and 11 of the two arms 7 and 8, a twisting or tilting of the closure device 13 during the moving-in step is thereby prevented. As can be seen from FIG. 3, the respective guide rib 18 of the tension element 14 is provided with a cut-out 31 whereby it is achieved that the locking element 15 can be rotated with respect to the tension element 14 about the axis of the tension screw 16 over the respective guide rib 18. During the turning or locking of the locking element 15, the respective guide ribs 17 serve as stop 32; the locking position is reached when the locking element 15 abuts against these stops 32.

Shown in FIG. 4 is the state in which the closure device 13 is put on the head part 3 of the pedicle screw 1, but is not yet locked. The locking element 15 is situated in the correct position with respect to the pedicle screw 1, owing to the guided position of the tension element 14 between the two arms 7 and 8. To lock, the locking element 15 can now be simply rotated clockwise; the projections 21 provided on the collar 20 end up correctly in the groove 12. To move these projections 21 into the groove 12, the respective projection 12 passes through the cut-out 31 provided on the respective guide rib 18 of the tension element 14.

The situation where the locking element 15 has reached the locking position is shown in FIG. 5. The locking element 15 hereby abuts in each case against the stop 32 provided on the guide rib 17 of the tension element 14.

When a pedicle screw is inserted into the vertebral body of a vertebral column, the rod 33 is of course inserted before placement of the closure device 13, as can be seen in the sectional drawing according to FIG. 6. In the sectional drawing according to FIG. 6, the closure device 13 is shown in the state of being placed on the pedicle screw 1. The locking element 15 is situated in the locking position, as is shown in FIG. 5. In this position, the tension screw 16 can now be tightened. Upon tightening of this tension screw 16, the support surface 27 of the tension screw 16 presses on the surface 30 of the tension element 14. The tension element 14 is hereby pressed against the rod 33. The resulting counterforce is transmitted via the locking element 15 and via the projections 21 to the head part 3 of the pedicle screw 1. The rod 33 is thus braced in the U-shaped recess 4 and in the tension element 14. Achieved at the same time is that the locking element 15 is secured against rotating backwards. The rod 33 is thereby secured in the head part 3 of the pedicle screw 1 in an optimal way.

Since the locking element 15 encloses the two arms 7 and 8 of the U-shaped recess 4 from the outside, these two arms 7 and 8 are kept in the correct position even in the tensioned state, i.e. a spreading apart of the two arms 7 and 8 is rendered impossible. The head part 3 of this pedicle screw 1 can thus be constructed very compactly. In particular, the height can be kept very minimal.

As shown in FIG. 7, the bottom surface 9 connecting the inner surfaces of the arms 7 and 8 in this pedicle screw 1 is provided with ridges 34 and grooves 35 running transversely with respect to the rod 33. The rod 33 has corresponding ridges 36 and grooves 37. Also the tension element 14 is provided with corresponding ridges 38 and grooves 39. In the state of the rod 33 being inserted in the U-shaped recess 4, the ridges 34 of the pedicle screw engage in the grooves 37 of the rod, while the ridges 36 of the rod engage in the corresponding grooves 35 of the pedicle screw. Correspondingly, the ridges 38 of the tension element engage in the grooves 37 of the rod, while the ridges 36 of the rod 33 engage in the grooves 39 of the tension element 14. A formfitting connection is thus obtained between pedicle screw 1, rod 33 and tension element 14, or respectively the closure device 13. This is especially advantageous when the rod is made of an elastic material, for example a polyurethane-based biocompatible plastic.

Pedicle screws of this kind as well as the closure device are usually made of a titanium alloy. Of course other suitable materials would also be conceivable.

In the embodiment example shown in the drawings, pedicle screw 1 and tension element 14 of the closure device 13 as well as the rod 33 are provided with corresponding ridges and grooves. Of course the respective surfaces could be smooth, in particular if a relatively rigid rod, made for instance of a titanium alloy, is used. When securing this rod having a smooth surface in the pedicle screw, a pure friction connection is obtained, which, however, likewise results in a secure anchorage by corresponding tightening of the tension screw.

With this design, a pedicle screw with closure device is obtained with which both elastic rods and rigid rods can be secured in the respective pedicle screw in an optimal way. By means of the design shown, a very compact construction is achieved. Moreover the insertion of the rod in the pedicle screw, the fitting of the closure device, the locking and the tensioning are very easily feasible and require only very simple tools.

The invention claimed is:

1. A pedicle screw with a closure device for securing a rod for stabilization of vertebral column, comprising a screw-in part, a head part provided on the screw-in part, a U-shaped recess disposed in the head part, which recess is formed by inner surfaces of two arms and a bottom surface connecting the two inner surfaces, in which recess the rod is insertable and is held by the closure device; wherein the closure device comprises a yoke-shaped locking element which has a collar on each of two end regions opposite each other, on each of which collars projections are provided, said projections being directed toward each other, a groove is provided outside on each of the two arms running transversely to these arms such that the yoke-shaped locking element is placeable on the arms and is rotatable, and, to reach a locking position, the projections each end up in the corresponding groove;

wherein a tension screw is screwed into the yoke-shaped locking element, and the tension screw is connected in a rotatable way to a tension element, so that the tension screw, the locking element and tension element are connected as one unit;

wherein the tension element is insertable in a guided way between the arms, and, in the locked position of the locking element, is able to be tensioned, by means of the tension screw, against the rod inserted in the recess; and wherein the tension screw has a threaded part that is extended by a bolt piece, and a support surface on the tension screw is formed between the threaded part and the bolt piece.

2. The pedicle screw with a closure device according to claim 1, wherein the locking position of the yoke-shaped locking element is predefined in the head part by means of limit stops.

3. The pedicle screw with a closure device according to claim 1, wherein the tension element is provided with guides, by means of which the tension element is placeable on the two arms of the head part in a guided way.

4. The pedicle screw with a closure device according to claim 3, wherein the guides consist of guide ribs provided on the tension element, which co-operate with guide surfaces provided on the arms.

5. The pedicle screw with a closure device according to claim 1, wherein the tension element is provided with a central bore, into which the bolt piece of the tension screw protrudes, and the end region of the bolt piece remote from the threaded part is provided with a flange, so that the tension element is rotably connected to the tension screw.

6. The pedicle screw with a closure device according to claim 1, wherein the support surface is supported on a surface correspondingly provided on the tension element.

7. The pedicle screw with a closure device according to claim 1, wherein the rod is made of an elastic material, a cylindrical surface of which is provided with ridges and grooves, and the bottom surface connecting the inner surfaces of the arms and the surface of the yoke-shaped locking element turned toward the rod are provided with corresponding ridges and grooves.

8. The pedicle screw with a closure device according to claim 7, wherein the elastic rod is made of a biocompatible plastic.

9. The pedicle screw with a closure device according to claim 8, wherein the biocompatible plastic is a polyurethane-based material.

* * * * *